United States Patent [19]

Nienart

[11] 3,958,728
[45] May 25, 1976

[54] ORTHOPEDIC BANDAGE CORE
[75] Inventor: Louis F. Nienart, Elizabeth, N.J.
[73] Assignee: Allied Chemical Corporation, New York, N.Y.
[22] Filed: June 24, 1974
[21] Appl. No.: 482,529

[52] U.S. Cl. .............................. 222/519; 128/269
[51] Int. Cl.² ...................................... B65D 41/04
[58] Field of Search ................... 222/187, 519, 521; 128/269, 260; 242/55.55; 239/52, 55; 132/42 R

[56] References Cited
UNITED STATES PATENTS

| 2,529,004 | 11/1950 | Eley | 222/519 X |
| 3,067,916 | 12/1962 | Lerner | 222/519 |
| 3,140,799 | 7/1964 | Mehr | 222/519 X |
| 3,324,855 | 6/1967 | Heimlich | 128/269 |

FOREIGN PATENTS OR APPLICATIONS

| 588,080 | 1/1925 | France | 222/519 |

Primary Examiner—Robert B. Reeves
Assistant Examiner—John P. Shannon
Attorney, Agent, or Firm—Roger H. Criss; A. J. Plantamura

[57] ABSTRACT

A fluid dispensing device comprising (a) a housing having a closed end, and opposite open end and fluid release opening extending through the wall of the housing; (b) an inner member adapted to contain a fluid and having one open end, an opposite closed end, a length substantially coextensive with the length of said housing and an outside cross-sectional dimension smaller than the inside cross-sectional dimension of the housing; the open end of the inner member being insertable in the open end of the housing thereby providing an annular space between the wall of the housing and the inner member; (c) the open end of the inner member being engageable with the closed end of the housing so as to form a first releasable seal to contain the fluid in the inner member; and (d) threads provided on the inner member adjacent its closed end and engageable with threads provided on the housing adjacent its open end so as to form a second releasable seal.

10 Claims, 2 Drawing Figures

U.S. Patent May 25, 1976 3,958,728
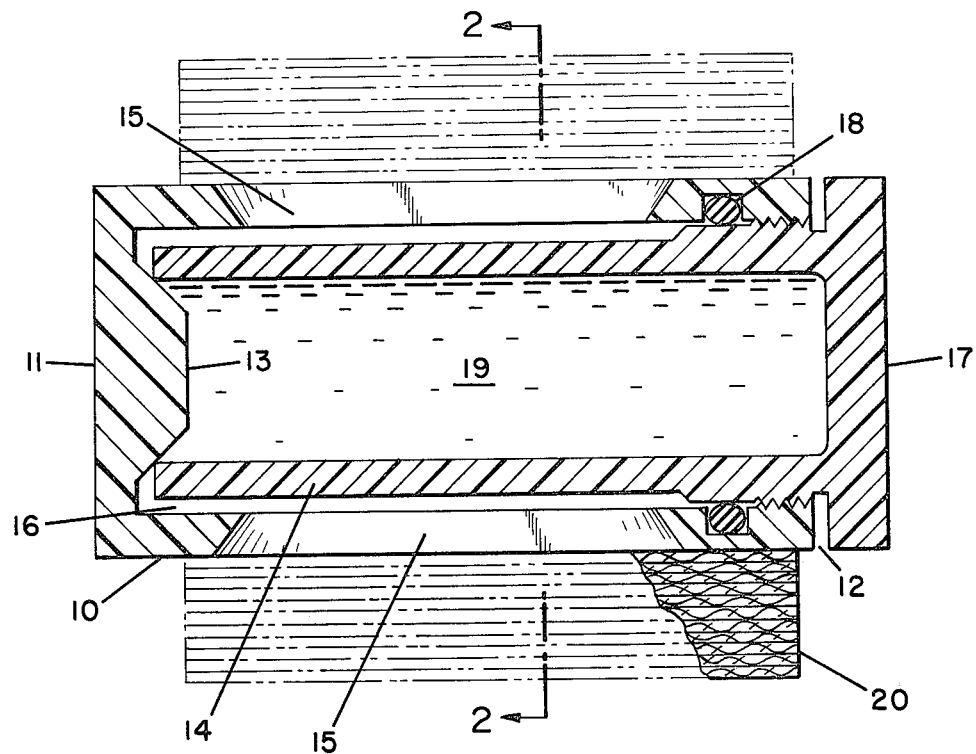
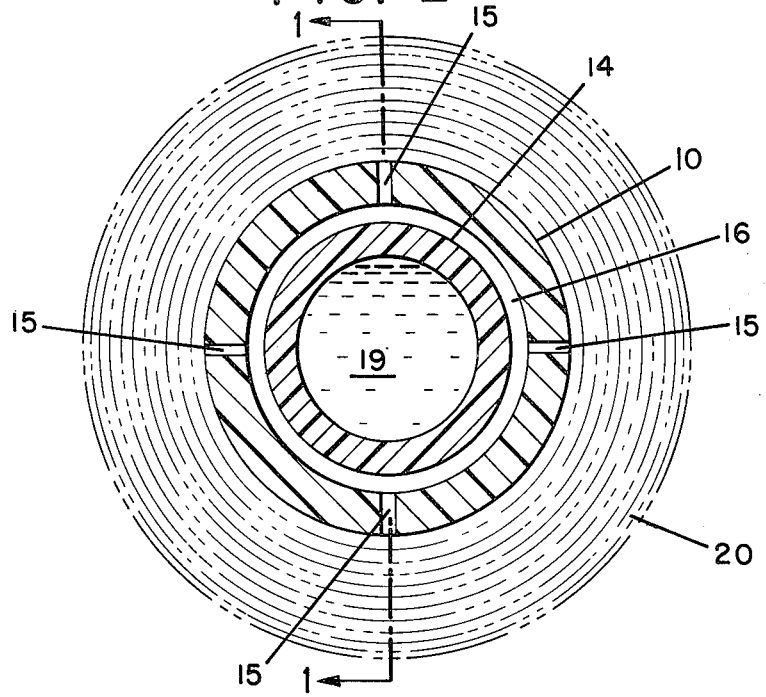

ORTHOPEDIC BANDAGE CORE

SUMMARY OF THE INVENTION

This invention relates to a fluid dispensing device, in particular, the invention is directed to a fluid dispensing device which is enclosed by an absorbent material onto the surface of which the fluid is to be dispensed.

For certain applications, it is necessary to wet an absorbent material with a fluid solution. Due to a variety of factors, such as the volatility of the solution, the reactivity of the solution with the material, etc., it may be desirable to apply the fluid immediately before use of the material rather than to store the previously wetted material. In accordance with the present invention, there is disclosed a novel fluid dispensing device which can be used in conjunction with an absorbent material to produce an easily storable, shapable, long shelf life package.

In accordance with this invention there is provided a fluid dispenser comprising (a) a housing having a closed end, an opposite open end and fluid release opening means extending through the wall of the housing; (b) an inner member adapted to contain a fluid and having one open end, an opposite closed end, a length substantially coextensive with the length of said housing and an outside crosssectional dimension smaller than the inside cross-sectional dimension of the housing; the open end of the inner member being insertable in the open end of the housing thereby providing an annular space between the wall of the housing and the inner member; (c) the open end of the inner member being engageable with the closed end of the housing so as to form a first releasable sealing means to contain the fluid in the inner member; and (d) means provided on the inner member adjacent its closed end and engageable with means provided on the housing adjacent its open end so as to form a second releasable sealing means.

A particular use for this novel fluid dispensing device is for the dispensing of a tertiary amine polymerization promoter/activator into a material preimpregnated with a monomer or prepolymer as disclosed in copending U.S. Application Ser. NO. 482,118, of Nienart et al. entitled "Lightweight Orthopedic Cast Material". That application is directed to a novel rigid orthopedic structure comprising a bandage preimpregnated with at least about 10% by weight of a member of the group consisting of a monomer of the formula:

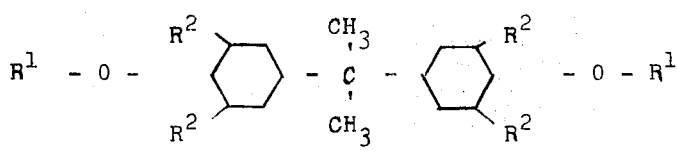

wherein $R^1$ is an acrylic substituent and each $R^2$ is the same and is H, $CH_2OH$ or $CH_2CH_2OH$, a prepolymer of said monomer and mixtures thereof, and cured by treating with a dual component curing system comprising a first curing component comprising an organic peroxide and a volatile solvent therefor and a second curing component comprising a tertiary amine polymerization promoter. The two curing components must be separately packaged and cannot be combined with the bandage prior to application since contact with the bandage would induce premature polymerization of the bandage material. When such orthopedic structure system is used in conjunction with the novel dispensing device of the present invention, the curing components comprising the polymerization promoter can be packaged in the fluid dispensing device, the preimpregnated bandage wrapped around the fluid containing device and the entire system sealed. At the point of application of the structure, it would only be required to dispense the promoter-containing fluid into the bandage, knead the bandage to distribute the solution, apply the bandage to the body member and apply, preferably by spraying, the remaining organic peroxide curing component. In addition to use with the novel cast system disclosed in the aforementioned application, the device of the present invention could also be used with any rigid plastic structure capable of being cured using known dual component curing systems.

BRIEF DESCRIPTION OF THE DRAWING

FIG. 1 represents an exploded, length-wise cross-sectional view of the device of the present invention.

FIG. 2 is a cross-sectional view of the device, taken along line 2–2 of FIG. 1.

DESCRIPTION OF THE PREFERRED EMBODIMENTS

In accordance with a preferred embodiment of this invention, and referring to FIGS. 1 and 2, there is shown a housing 10 having a closed end 11 and an open end 12. The housing may be of any shape although a cylindrical shape is preferred. In accordance with the embodiment shown in FIG. 1, the closed end 11 is molded or otherwise formed so as to include a tapered internal extension 13 adapted to engage with the fluid containing inner member 14 so as to form a leak-proof releasable sealing means. Similar molded bosses or chamfers could be constructed in the housing so as to effect a suitable sealing means. While the required releasable seal is preferably integrally formed in the housing, the seal may also be provided by positioning poly-caps, rubber gaskets, etc., within the closed end of the housing which will produce a leak-proof seal when in a closed position while permitting relatively unrestricted passage of fluid when open.

Housing 10 is also provided with a plurality of apertures 15 of any suitable size and shape, e.g., round, rectangular, oval, etc., located along the lengthwise wall of the housing through which the fluid will be dispensed when the device is utilized. These apertures can be arranged in any variety of designs such as a series of many relatively small apertures distributed throughout the length of the housing or as a few relatively larger slot-like apertures positioned along the length of the housing. In the particular embodiment shown, four slots 15 are positioned along the housing length in a substantially uniform distribution along the circumference of the housing as can be seen in FIG. 2. It is desirable that whatever the array of apertures chosen, they be positioned so as to provide a relatively uniform and equal flow of fluid from each aperture, thus resulting in uniform dispersing of the fluid throughout the entire material to be wetted.

Inner member 14 has one closed end 17 and an opposite open end. Inner member 14 may also be of any desired shape, although a cylindrical shape is preferred. Inner member 14 is insertable into housing 10 at its open end and is substantially coextensive in length with the housing. The outside dimension of inner member 14 (e.g., its outside diameter for cylindrical shapes) is sufficiently smaller than the inside dimension (e.g., diameter) of housing 10 so as to provide an annular space 16 between the inner wall of housing 10 and the outer wall of inner member 14. The open end of inner member 14 is adapted to engage closed end 11 of housing 10 such as the tapered portions of internal extension 13. When so engaged, a first releasable sealing means is formed which prevents release of a fluid 19 contained in inner member 14. Upon release (opening) of such releasable sealing means, fluid 19 will flow through annular space 16, into apertures 15 and out of the dispenser.

Means are provided adjacent closed end 17 of inner member 14 to engage with means provided on housing 10 adjacent its open end 12. When so engaged, a second releasable sealing means is formed between the housing and the inner member. This second releasable sealing means prevents escape of fluid 19 from the open end 12 of housing 10 when the first releasable sealing means is opened. Preferably, the second sealing means is provided by external threads on the outer wall of inner member 14 which engage and cooperate with corresponding internal threads on the inner wall of housing 10. While a threaded seal is preferred, other sealing means such as frictional seals may be employed.

Closed end 17 of the inner member is preferably in the form of a capped end. The capped end and the closed end of housing 11 may preferably be provided with suitable knurling or other means for ease of gripping and turning.

While it is not required within the broadest scope of the invention, it is desirable to position an additional sealing means 18 adjacent to the second releasable sealing means formed by the open end of the housing and the closed end of the inner member. In use, this additional sealing means assists in preventing the fluid from passing out of the open end of the housing when the first releasable sealing means between the two members is opened. Preferably seal 18 is an O-ring seal provided in the inner wall of housing 10 adjacent to the threaded mating sections.

It is desirable to fabricate the entire dispenser including seals, etc., from a plastic material such as polypropylene, ethylene-chlorotrifluoroethylene copolymer, etc. However any material which will provide ease of fabricating and be compatible with the solution with which it is to be filled may be used. Moreover, depending on the desired application, the container may be constructed of low cost plastic such as high density polyethylene, polystyrene, etc. such that it may be disposed of when empty. Alternately, a higher quality construction material may be used when it is desired to refill the device.

In use, the inner member 14 containing fluid 19, is inserted into the housing 10 and sealed therein by engagement of the open end of inner member 14 with extension 13 of housing 10 by engagement of the mating threaded sections and by O-ring seal 18. An absorbent material 20 such as bandage material or fabric is then wrapped around the sealed container. The entire system may be packaged, as for example, in an air tight container or polyethylene film. When use of the system is desired, the outer packaging is removed and the second releasable sealing means is partially released as, for example, by only a few turns of closed end 17. As a result, the first sealing means located at the closed end 11 of the housing is released. This permits fluid 19 to flow into the annular space 16 and out through the apertures 15 into the absorbent material 20. Seal 18 and the threaded mating sections prevent flow of the fluid through open end 12 of housing 10.

Accordingly, the second releasable sealing means need be only partially opened to dispense the fluid through the apertures. However, especially when the dispenser is intended to be refilled, the second releasable sealing means may be adapted to be completely opened, so as to totally release the inner member from the housing. This may be accomplished, for example, by further turning of closed end 17 of the inner member.

EXAMPLE

A dispensing device according to the present invention was constructed from an ethylene-chlorotrifluoroethylene copolymer. The device was provided with a tapered internal extension integrally formed in the closed end of a cylindrical housing, four slot-like apertures distributed along the length of the housing, threaded mating sections on the housing and cylindrical inner member to effect sealing and and O-ring located adjacent to the threaded section of the housing to provide an additional seal.

The inner member having an outer diameter of 7/16 inch was filled with 3.5 ml of a solution of cyclohexane containing 10% dimethyl-toluidine and a small quantity of blue dye. The filled member was inserted into a housing having an internal diameter of ½ inch. The device was tightly sealed and wrapped with 2 yards of 1½ inch width impregnated bandage. The threaded seal was then released about 1½ turns and the bandage kneaded for about one minute, during which time the dyed solution was observed to flow uniformly throughout the entire bandage.

Although certain forms of the present invention are shown and described herein in detail, other forms are possible. For example, a fabric layer having a nap surface may surround the dispenser and the dispenser may be filled with a dry cleaning fluid. Such a device may be used to remove stains from apparel or the like.

It is to be understood that variations and modifications of the present invention may be made without departing from the scope of the invention. It is also to be understood that the scope of the invention is not to be interpreted as limited to the specific embodiment disclosed herein, but only in accordance with the appended claims when read in light of the foregoing disclosure.

I claim:

1. A fluid dispenser comprising:
   a. a housing having a closed end, an opposite open end and fluid release opening means extending through the wall of said housing;
   b. an inner member adapted to store a fluid and having one open end, an opposite closed end, a length substantially coextensive with the length of said housing and an outside cross-sectional dimension smaller than the inside cross-sectional dimension of said housing; said open end of said inner member being insertable in said open end of said housing thereby providing an annular space between the wall of said housing and said inner member;

c. said open end of said inner member being engageable with said closed end of said housing so as to form a first releasable sealing means to contain said fluid in said inner member; and d. means provided on said inner member adjacent its closed end and engageable with means provided on said housing adjacent its open end so as to form a second releasable sealing means, the portion of said inner member extending from said open end of said inner member to said means adjacent the closed end of said inner member being adapted to store said fluid.

2. The dispenser of claim 1 wherein said releasable means is formed by the engagement of external threads provided on the outer wall of said inner member with internal threads provided on the inner wall of said housing.

3. The dispenser of claim 1 wherein said housing and said inner member are cylindrical in shape.

4. The dispenser of claim 1 wherein said fluid release opening means comprises a plurality of apertures.

5. The dispenser of claim 4 wherein said apertures are substantially uniformly distributed along the outside wall of said housing.

6. The dispenser of claim 1 wherein an additional sealing means is provided adjacent to said second releasable sealing means.

7. The dispenser of claim 6 wherein said additional sealing means comprises an O-ring seal.

8. The dispenser of claim 1 wherein said closed end of said housing is provided with a tapered internal extension and said first releasable sealing means is formed by engagement of said open end of said inner member with the tapered portion of said internal extension.

9. The fluid dispenser of claim 1 wherein said fluid comprises a polymerization promoter.

10. A package comprising the fluid dispenser of claim 1 wrapped with an absorbent material.

* * * * *